United States Patent [19]

Falk et al.

[11] Patent Number: 4,898,981

[45] Date of Patent: Feb. 6, 1990

[54] HETEROATOM CONTAINING PERFLUOROALKYL TERMINATED NEOPENTYL GLYCOLS AND COMPOSITIONS THEREFROM

[75] Inventors: Robert A. Falk, New City, N.Y.; Kirtland P. Clark, Bethel, Conn.; Athanasios Karydas, Brooklyn, N.Y.

[73] Assignee: Ciba-Geigy Corporation, Ardsley, N.Y.

[21] Appl. No.: 209,743

[22] Filed: Jun. 20, 1988

[51] Int. Cl.$^4$ .............................................. C07C 147/00
[52] U.S. Cl. .................................... 568/28; 568/29; 568/30; 568/31; 568/32; 568/46
[58] Field of Search ................... 568/46, 28, 29, 30, 568/31, 32

[56] References Cited

U.S. PATENT DOCUMENTS

| | | | |
|---|---|---|---|
| 2,965,659 | 12/1960 | Tiers | 260/408 |
| 2,972,638 | 2/1961 | Tiers | 260/653.1 |
| 3,088,849 | 5/1963 | Friedlander | 117/127 |
| 3,145,222 | 8/1964 | Brace | 260/408 |
| 3,478,116 | 11/1969 | Smeltz | 260/433 |
| 3,544,663 | 12/1970 | Hauptschein et al. | 260/900 |
| 3,578,701 | 5/1971 | Smeltz | 260/185 |
| 3,655,732 | 4/1972 | Scriver | 260/486 |
| 3,728,151 | 4/1973 | Sherman et al. | 111.7/138.8 |
| 3,758,447 | 9/1973 | Falk et al. | 260/78.5 |
| 3,838,165 | 9/1974 | Blochl | 260/309.7 |
| 3,935,277 | 1/1976 | Dear et al. | 260/609 R |
| 4,001,305 | 1/1977 | Dear et al. | 260/486 |
| 4,046,944 | 9/1977 | Mueller et al. | 428/262 |
| 4,054,592 | 10/1977 | Dear et al. | 560/25 |
| 4,097,642 | 6/1978 | Dear et al. | 428/262 |
| 4,099,642 | 7/1978 | Nergard | 220/254 |
| 4,584,143 | 4/1986 | Falk | 558/240 |

OTHER PUBLICATIONS

Chem. Abst., 88, 61965g, (1978).
Chem. Abst., 68, 115832u, (1968).
Chem. Abst., 87, 68358z, (1977).

*Primary Examiner*—Maurice J. Welsh
*Attorney, Agent, or Firm*—Luther A. R. Hall

[57] ABSTRACT

Heteroatom containing perfluoroalkyl terminated neopentyl glycols of the formula $HO[-CH_2C(CH_2X-E-R_f)_2CH_2O]_{1-3}-H$ prepared from halogenated neopentyl glycols and thiols of the formula $R_f-E-SH$, or amines of the formula $R_f-E-NH-R$ wherein $R_f$ is a hydrophonic, olephobic fluoroaliphatic group of up to 20 carbon atoms, E is alkylene of up to 10 carbon atoms, optionally interrupted by up to three groups including $-NR$, $-O-$, $-S-$, $-SO_2-$, $-O_2C$, CONR, and $-SO_2NR$, and X is $S, SO_2$ or $NR_2$, where R is independently hydrogen, alkyl, or hydroxyalkyl of 1 to 6 carbon atoms are described.

The polymeric reaction products of said fluorinated diols, and optionally other diols with isocyanates to prepare polyurethanes; with amines and isocyanates, to prepare polyureas/polyurethanes; with acids or derivatives, to prepare polyesters or polycarbonates are disclosed. These include polymeric, random or block urethane, and/or urea, and/or ester compositions containing the residue of at least one $R_f$-neopentyl glycol containing two perfluoroalkylhetero groups.

These polymeric compositions provide improved thermal stability and useful low surface energy coatings with oil, water repellency and soil-release properties for textiles, glass, paper, leather and other materials.

12 Claims, No Drawings

HETEROATOM CONTAINING PERFLUOROALKYL TERMINATED NEOPENTYL GLYCOLS AND COMPOSITIONS THEREFROM

BACKGROUND OF THE INVENTION

This invention relates to hetero group containing perfluoroalkyl terminated neopentyl glycols and their derived polymeric compositions and use to impart oil and water repellency to textiles, glass, paper, leather, and other compositions.

Certain bis-perfluoroalkyl terminated neopentyl glycols devoid of sulfur or nitrogen heteroatoms have been described in U.S. Pat. Nos. 3,478,116 and 3,578,701. However, such compounds are difficult and expensive to prepare and therefore are impractical intermediates from which to obtain useful products. Additionally, other bis-perfluoroalkyl glycols containing sulfur are described in U.S. Pat. Nos. 3,935,277, 4,001,305, 4,054,592, 4,099,642, and 4,046,944. These compounds are not readily obtainable in high purity and are thermally unstable. The subject perluoroalkyl glycols are readily isolated in high yield and purity and are thermally stable. Another advantage of the subject glycols is that the pendant perfluoroalkyl chains are connected by flexible nitrogen or sulfur heteroatoms to the remainder of the molecule thus providing more mobile perfluoroalkyl functions.

Bis-perfluoroalkyl glycols and polymeric derivatives thereof are useful because they possess a low free surface energy which provides oil and water repellency to a wide variety of substrates. Glycols containing a single $R_f$-function are known but do not provide these properties to the same extent. The subject glycols may be prepared in high yield and purity in contrast to prior art materials. Most importantly the instant glycols are thermally stable.

DETAILED DISCLOSURE

One aspect of this invention relates to a method of making such $R_f$-glycols. Another aspect of this invention relates to derived $R_f$-containing polyurethane-/polyurea/ or polyester-containing compositions. One embodiment of this invention relates to hydroxyl terminated prepolymers of the $R_f$-glycol prepared from polyisocyanates, lactones or isocyanate terminated prepolymers. If desired, $R_f$-glycols can be converted to isocyanate terminated prepolymers to form reactive compositions with alcohols, polyols, polyamines, $R_f$-glycols, polyol prepolymers and hydroxyl terminated $R_f$-containing prepolymers. In another embodiment, the $R_f$-glycols can be used to replace part or all of the hydroxyl component in a urethane composition.

Another embodiment of such polymeric compositions relates to reactive compositions comprising aliphatic polyester segments comprised of the subject $R_f$-neopentyl glycol reacted with dicarboxylic acids, esters, anhydrides, lactones or acid chlorides, the mole ratios being adjusted to obtain the desired hydroxy or carboxyl end group functionality. In another embodiment suitable functionally terminated polyester polyols as described, for example, in Encyclopedia of Polymer Science and Technology, Interscience Pub., 11 (1969), p. 513 can be linked with the $R_f$-diol to form the polyesters of this invention. Alternately, the $R_f$-diol can be coreacted with the polyester precursor reagents, e.g., dicarboxylic acid and aliphatic diol, under esterification conditions. The fluorochemical polyesters can also be derived from isocyanate containing prepolymers, e.g. isocyanate end-capped $R_f$-glycol and hydroxy terminated polyester segments as described herein.

In another embodiment, the polymers are more appropriately defined as block polymers and contain 15-70% of a fluorochemical block connected to a hydrophilic block of 30-85% by weight. These blocks are most preferably connected by urea linkages in the final product condensate and are useful as coatings on textiles, glass, linoleum, leather, wood, tile, metals, plastics, and various materials. They are of of particular use on textile materials as soil release agents, showing increased durability as compared to urethane-connected condensation block polymers.

This invention most generally relates to novel heteroatom containing perfluoroalkyl terminated neopentyl glycols and derived polymeric urethane, and/or urea and/or ester linked compositions containing said $R_f$-glycols.

Another aspect of this invention relates to a substrate containing 0.01 to 10% by weight of a fluorine-containing urethane and/or urea, and/or ester composition, at least part of said fluorine being provided by one or more units derived from the heteroatom containing $R_f$-neopentyl glycol.

The novel heteroatom containing $R_f$-neopentyl glycols have the general formula I

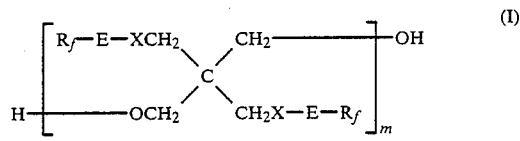

where
$R_f$ is straight or branched chain perfluoroalkyl of 1 to 18 carbon atoms or said perfluoroalkyl substituted by perfluoroalkoxy of 2 to 6 carbon atoms.
E is branched or straight chain alkylene of 1 to 10 carbon atoms, or said alkylene interrupted one up to three groups including —NR; —O—, —S—, —SO$_2$—, —CO$_2$—, —O$_2$C—, —CONR—, and —SO$_2$NR—, X is S, SO$_2$ or —NR—, where R is independently hydrogen, alkyl or hydroxyalkyl of 1 to 6 carbon atoms, and m=1–3.

It is understood that the $R_f$ group usually represents a mixture of perfluoroalkyl moieties. When the $R_f$ group is identified as having a certain number of carbon atoms, said $R_f$ group also usually concomitantly contains a small fraction of perfluoroalkyl groups with lower carbon atoms and a small fraction of perfluoroalkyl groups with higher carbon atoms.

Preferably the instant compounds of formula I are those where $R_f$ is perfluoroalkyl of 2 to 12 carbon atoms or perfluoroalkyl of 2 to 6 carbon atoms substituted by perfluoroalkoxy of 2 to 6 carbon atoms, E is alkylene of 2 to 6 carbon atoms, —CONHCH$_2$CH$_3$—, —CH$_2$CH$_2$N(CH$_3$)CH$_2$CH$_2$—, —CH$_2$CH$_2$SO$_2$NHCH$_2$CH$_2$— or SO$_2$NHCH$_2$CH$_2$—, X is —S— or SO$_2$—, and m is 1 or 2.

Most preferred are those compounds where $R_f$ is perfluoroalkyl of 6 to 12 carbon atoms, E is ethylene, m=1, and X is S, i.e.,

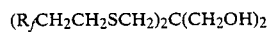

In another group of most preferred compounds $R_f$ is perfluoroalkyl of 6 to 12 carbon atoms, E is ethylene, m=2, and X is S i.e. 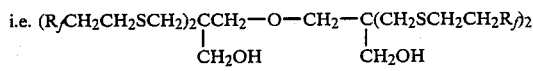

The novel $R_f$-glycols can be obtained directly by the reaction of a perfluoroalkyl thiol of formula $R_f$—E—SH or a perfluoroalkyl amine of formula $R_f$—E—$NR_2$ with a dihalogenated pentaerythritol of formula $(YCH_2)_2C(CH_2OH)_2$,
or a dipentaerythritol of formula $HO[CH_2C(CH_2)_2CH_2O]_2H$,
where Y is Cl, Br, or I.

In one preferred embodiment, the neopentyl derivative is dibromopentaerythritol and has the formula $(BrCH_2)_2C(CH_2OH)_2$. In another preferred embodiment tetrabromodipentaerythritol $HO[CH_2C(CH_2Br)_2CH_2O]_2H$, is used. These intermediates are commercially available in high purity; dichloro and iodo neopentyl glycols have also been reported.

The synthesis of $R_f$-diols proceeds by the nucleophilic substitution of a perfluoroalkyl substituted thiolate or amine for halide. The reaction may be conducted in an aqueous system using phase transfer catalysis, but work-up of such an aqueous product is difficult due to troublesome emulsions. The improved process of this invention involves the combination of:

a. an aprotic solvent, such as N-methylpyrrolidone, N,N-dimethylformamide, dimethyl sulfoxide, or the like, or ketones, such as acetone, methyl alkyl ketones, or dialkyl ketones. Chlorinated solvents and esters generally give poor conversions and are unsuitable;

b. moderate reaction temperatures, on the order of 50° to about 120° C.; and c. a stoichiometric quantity of an anhydrous alkaline earth carbonate, preferably potassium carbonate, in the ratio of 1 mol carbonate per mol of halogen to be displaced; and d. in the case of the amines, tertiary amine catalysis is useful as exemplified by triethylamine, tributylamine, dimethylaminopyridine, or piperidine.

The reaction temperature, and choice of solvent are mutually dependent. A reaction temperature in the range of 50°–140° C. is one wherein the formation of undesirable by-products is minimized and wherein the reaction products are stable.

Conditions are adjusted in order to achieve a reasonable rate of reaction at the chosen temperature.

In the synthesis of the $R_f$-glycols a number of by-products may be present. These are derived in part from trace impurities present in the diol and in part as reaction intermediates. When the starting thiol is $R_f$—$CH_2CH_2SH$ and dibromoneopentyl glycol is used these by-products include

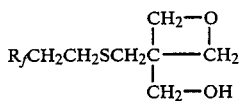

$R_f CH_2CH_2SCH_2C(CH_2OH)_3$ and
$R_f CH_2CH_2SCH_2C(CH_2OH)_2CH_2Br$

Such intermediates and the oxetane formation are consistent with the general reaction conditions.

It should be noted that the ready oxidation of thiols to disulfides requires that the chemistry be conducted in an inert atmosphere.

The subject diols can also be made by first reacting the bromodiol intermediates with a functional thiol or amine, e.g. $HSCH_2CH=CH_2$, $HSCH_2COOH$ or $NH_2CH_2CH=CH_2$. The resultant sulfide or amine can then be reacted with the $R_f$-containing moiety by a suitable chemistry which does not involve the pendant hydroxyl groups.

For example,

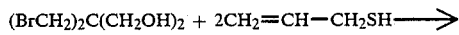
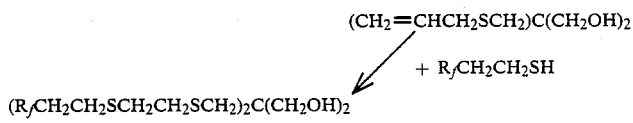

An alternate synthesis has also been demonstrated. Dibromoneopentyl glycol can be converted to 2,6-dioxaspiro [3.3] heptane as reported by Abdun—Nur and Issidorides in J. Org. Chem. 27, 67–69 (1962), and this intermediate converted to $R_f$-diol.

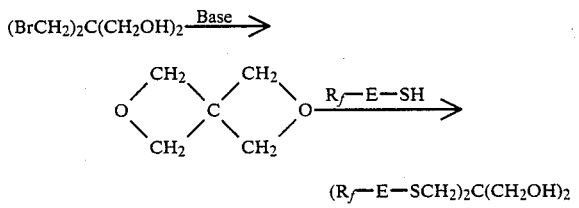

This synthetic approach is less favorable since the volatile spiro-oxetane must first be isolated. Attack by the thiolate nucleophile occurs readily on the spiro compound, but the resultant oxetane reacts with difficulty. The process involves the combination of:

a. a solvent in which the spiro-oxetane is soluble, preferably n-butanol;

b. reaction temperatures of 55°–150° C. The reaction temperature is kept low initially to avoid volatilization of the oxetane and is increased as the reaction proceeds, and c. a basic catalyst, e.g. sodium methoxide or potassium t-butoxide.

The reaction temperature and solvent are mutually dependent. Under appropriate conditions with n-butanol, at 55°/4.5 hours (½ thiol charge) and then 125°/16.5 hours (remainder of thiol charge), the product formed assayed 17% monoadduct, 78% diadduct.

The subject sulfido-linked diols can be readily oxidized to the corresponding bis-sulfone diols by peracetic acid ($H_2O_2$/acetic acid) or by other conventional oxidants which selectively oxidize sulfides in the presence of alcohol functions. With peracetic acid, temperatures of 30°–100° C. are appropriate depending on the amount of excess oxidizing agent to ensure that the intermediate sulfoxides are completely oxidized.

Perfluoroalkyl thiols useful herein are well documented in the prior art. For example, thiols of the formula $R_f$—E—SH have been described in a number of U.S. Patent Nos. including U.S. Pat. Nos. 3,655,732 and 4,584,143.

Thus, U.S. Pat. No. 3,655,732 discloses mercaptans of formula $$R_f-E-SH$$

where E is alkylene of 1 to 16 carbon atoms and $R_f$ is perfluoroalkyl, and teaches that halides of formula $R_f$—E-Halide are well-known; reaction of $R_fI$ with ethylene under free-radical conditions gives $R_f(CH_2CH_2)_aI$ while reaction of $R_fCH_2I$ with ethylene gives $R_fCH_2(CH_2CH_2)_aI$ as is further taught in U.S. Pat. Nos. 3,088,849; 3,145,222; 2,965,659 and 2,972,638.

U.S. Pat. No. 3,655,732 further discloses compounds of formula $$R_f-R'-Y-R''-SH$$

where R' and R" are alkylene of 1 to 16 carbon atoms, with the sum of the carbon atoms of R' and R" being no greater than 25; $R_f$ is perfluoroalkyl of 4 through 14 carbon atoms and Y is —S— or —NR'''— where R''' is hydrogen or alkyl of 1 through 4 carbon atoms.

U.S. Pat. No. 3,544,663 teaches that the mercaptan $$R_fCH_2CH_2SH$$

where $R_f$ is perfluoroalkyl of 5 to 13 carbon atoms, can be prepared by reacting the perfluoroalkyl alkylene iodide with thiourea or by adding $H_2S$ to a perfluoroalkyl substituted ethylene ($R_f$—CH=$CH_2$), which in turn can be prepared by dehydrohalogenation of the halide $R_f$—$CH_2CH_2$— halide.

The reaction of the iodide $R_f$—E—I with thiourea followed by hydrolysis to obtain the mercaptan $R_f$—E—SH is the preferred synthetic route. The reaction is applicable to both linear and branched chain iodides.

Particularly preferred herein are the thiols of formula $$R_fCH_2CH_2SH$$

where $R_f$ is perfluoroalkyl of 6 to 12 carbon atoms. These $R_f$-thiols can be prepared from $R_fCH_2CH_2I$ and thiourea in very high yield.

Perfluoroalkylamines useful herein are well documented in the prior art. For example, $C_6F_{13}CH_2CH_2NH_2$ has been described in Japan Kokai 77/118,406. $R_fCH_2NH_2$ wherein $R_f$ is $CF_3$ through $CF_3(CF_2)_{11}$ are described in British Patent No. 717,232 (1954).

Further $R_fSO_2NR(CH_2)_nNR(CH_2)_3NH_2$ and $R_fCH_2CH_2SO_2NH(CH_2)_nNR_2$ are described in G.B. No. 1,106,641 and U.S. Pat. No. 3,838,165 respectively; $R_fCONH(CH_2)_nNH_2$ in Jap. Kokai No. 52/14767.

The diols, can be used directly or indirectly to make a variety of condensation products such as polyesters, polyureas, polycarbonates, polyurethanes and the like. Polyurethanes are particularly preferred.

As used herein the term "urethane composition" means compounds and compositions which contain the characteristic

linkage and at least one $R_f$-containing group of formula

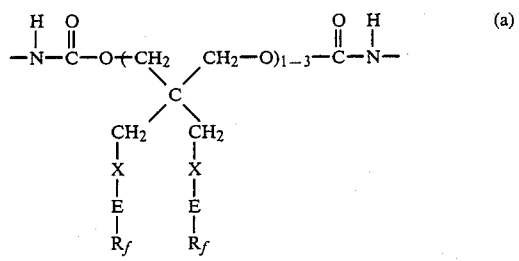

where $R_f$, X and E are as previously described.

Preferred urethane compositions include those where $R_f$, and E have the configurations previously described as being preferred and X is S.

The $R_f$-glycols can be used to make a wide variety of urethane intermediate and end products including hydroxyl and isocyanate-terminated prepolymers, low molecular weight urethane compositions useful to render plastics soil repellent, and high molecular weight compositions useful as elastomers, foams, paints and varnishes, and textile treating compositions. It is also possible to modify these $R_f$-containing urethane compositions so that they are water soluble or self-emulsifiable, a property that is particularly useful in connection with the textile treating compositions. Block polymer compositions of the $R_f$-containing diols and hydrophilic blocks have special utility in the textile industry as soil-release agents.

These compositions have extremely low free surface energies and therefore, possess oil and water repellent properties, as well as mold release and other properties associated with low free surface energy. It should be noted that the compositions of this invention are characterized by the presence of two perfluoroalkylhetero groups in close proximity, a characteristic which provides improved oil and water repellent properties over the fluorinated compositions of the prior art. Further the two perfluoroalkylthio groups are connected via a neopentyl moiety which does not permit the thermal elimination of mercaptan by β-elimination. Hence, these $R_f$-diols and derivatives have enhanced thermal stability. The β-elimination reaction of prior art sulfur containing $R_f$-diols as disclosed in U.S. Pat. No. 4,097,642 is shown in the following equation.

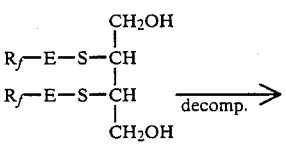

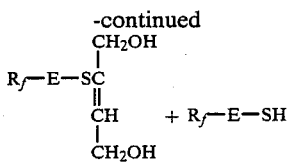

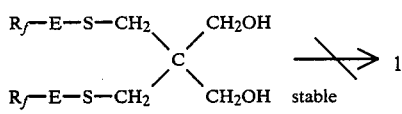

Using the $R_f$-compounds and compositions described herein, it is possible to manufacture molds that display the excellent release properties characteristic of silicone polymers. It is also possible to prepare polymeric compositions with enhanced thermal stability.

ELASTOMERS

Polyurethane elastomers generally have remarkable resistance to most solvents including gasoline, aliphatic hydrocarbons and, to some degree, aromatic hydrocarbons. They also exhibit excellent abrasion resistance. by inclusion of the $R_f$-glycol in an elastomer formulation, it is possible to increase the solvent resistance of urethane elastomers. The elastomers generally involve the reaction product of a diisocyanate, a linear long chain diol and a low molecular weight chain extender such as a glycol, diamine or polyol. Today, elastomers are generally prepared by a prepolymer technique whereby a diisocyanate is reacted with a hydroxyl-terminated polyester or polyether to form an isocyanato-terminated prepolymer. This prepolymer is then further reacted (chain extended) with a glycol, diamine or polyfunctional polyol (e.g. trimethylolpropane). Following the chain extension step, the liquid material solidifies and is removed from a mold and cured at elevated temperatures.

Urethane foams are usually prepared from diisocyanates and hydroxyl-terminated polyethers or polyesters. Linear or slightly branched polymers are used to provide flexible foams while more highly branched polymers produce rigid foams. Foaming is often accomplished by including water in the system, the reaction between isocyanate and water providing carbon dioxide for foaming. For rigid foams a low-boiling liquid such as trichlorofluoromethane has been used as a blowing agent.

Appropriate selection of catalysts, stabilizers, surfactants and other additives controls the foam formation, cell size and type, density, cure and the like. By incorporating the $R_f$-glycol into urethane foams, especially molded foams, it is possible to achieve improved mold release properties in rigid, semi-rigid and flexible foams. It is also possible to improve the water and solvent resistance of foams used as insulation.

COATINGS

Incorporation of the $R_f$-glycols into polyurethane coatings such as paints and varnishes improves the water and solvent resistance thereof. Widely used systems include the two-component coatings wherein a non-volatile isocyanate derived from the reaction of tolylene diisocyanate with a polyol, such as trimethylolpropane, is reacted with a polyfunctional polyester. Another system in use involves the one-component polyurethane coatings which are based on stable isocyanate-terminated prepolymers obtained from a diisocyanate such as tolylene diisocyanate and a polyfunctional polyether. Such coatings dry by the reaction of the free isocyanate groups with water or atmospheric moisture. The reaction proceeds through the unstable carbamic acid, with $CO_2$ being eliminated, to give primary amine groups which further react with isocyanate groups to form ureas.

Treatment of a textile with a fluorine-containing composition, notably a fluorine-containing polymer, provides oil and water-repellent characteristics thereto. Such compositions containing the residue of the $R_f$-glycol display improved oil and water repellence on textile substrates.

In higher molecular weight urethane compositions, linear polymer, obtained by reacting an $R_f$-glycol with an organic diisocyanate, having recurring structural units of formula

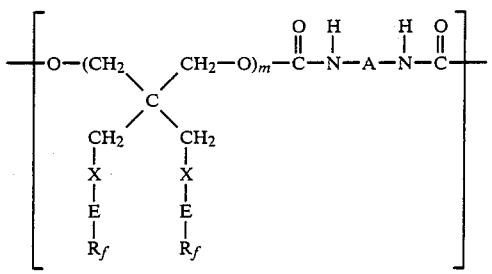

where $R_f$, E and X are as previously defined, where m is 1 or 2, and A is a divalent organic radical, preferably alkylene of 2 to 16 carbon atoms, cycloalkylene of 6 to 15 carbon atoms, unsubstituted or substituted phenylene or naphthylene or unsubstituted or substituted biphenylene or bisphenylene are useful as plastics, fibers, coatings and the like.

SOIL RELEASE AGENTS

The treatment or modification of fabrics to improve their properties is routine practice in the textile industry. However, resin-treated durable press garments are difficult to clean because they are prone to soil retention. Investigation of this phenomenon showed that resin treated cotton as well as the synthetic fibers are oleophilic and accordingly, dirt, particularly oily stains, clings tenaciously to the fabric substrate and is extremely difficult to remove under normal home washing conditions.

In an effort to overcome the soil removal resistance of resin-treated fabrics, artisans have commonly treated such fabrics with a hydrophilic colloid such as carboxymethyl cellulose and synthetic polymers such as polyacrylic acid and copolymers of acrylic acid with lower alkyl acrylates and methacrylates. These materials, which are referred to as soil release agents, apparently coat the textile fibers with a hydrophilic film which allows the fibers to be wet effectively by detergent solutions so that the soils are readily removed by laundering.

The combination of oleophobic fluorinated groups and hydrophilic poly(ethyleneoxide) containing groups in one polymer to achieve the release of oil stains from textiles has been described in U.S. Pat. Nos. 3,728,151 and 3,758,447. The advantage of fluorinated soil release agents over non-fluorinated ones stems from their oleophobic nature, which (a) prevents the wicking of oil stains into the fabrics and (b) facilitates the lifting off of the staining material from the fabric when it is washed.

It has also been reported that certain segmented (block) polyurethane/polyureas are useful soil-release agents—see U.S. Pat. No. 4,046,944.

The oleophobic blocks are comprise of fluorinated aliphatic groups held together in segments directly or through linkages made up of various combinations of functional groups and/or hydrocarbon chains. The preferred hydrophilic segments are based o polyoxyalkylene glycols or end-capped derivatives thereof. The molecular weight of the glycols may range from about 150 to 10,000 or more and may be repeated from 1 to 500 or more times.

A preferred embodiment of this invention is that a great increase in performance, especially in durability of fluorochemical textile finishes, can be achieved by use of polymer condensates, wherein the oleophobic and hydrophilic blocks are preferably connected by urea linkages rather than urethane linkages. A block polymer comprising oleophobic fluorinated blocks and hydrophilic poly(ethyleneoxide) blocks connected by urea linkages and having increased durability when applied to materials such as textiles is thus provided.

The fluorinated condensation polymers are made up of a combination of Blocks I and II:

Most urethane compositions that are used commercially to any great extent are copolymers that contain only a relatively small number of urethane linkages. These copolymers are prepared from a variety of segments, typically based on polyethers and polyesters and can have a molecular weight of from 200 to 10,000, generally from about 200 to about 4,000. By the inclusion of an appropriate amount of $R_f$-glycol in the starting materials, it is possible to prepare prepolymers that, when incorporated as part of a urethane composition favorably affect the properties thereof. It is similarly possible to incorporate a desired amount of $R_f$-glycol into the reaction mixture of a conventional prepolymer and an isocyanate so as to obtain conventional urethane compositions containing the divalent residue of the $R_f$-glycol. In the same way, there can be added an $R_f$-containing prepolymer together with or instead of the $R_f$-glycol.

The $R_f$-containing prepolymers can be hydroxy-terminated or isocyanate-terminated and, as indicated, can have a molecular weight as high as 10,000 although a molecular weight of 200 to about 4,000 is more usual.

Hydroxy-terminated prepolymers can be prepared by reacting an excess of a polyhydroxy component with a polyfunctional hydroxy-reactive component such as a polyisocyanate; an isocyanate-terminated prepolymer; a

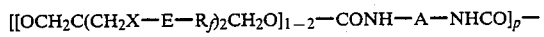

Block I

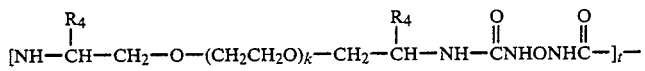

Block II

In these structures:

$R_f$ is derived from the subject $R_f$-glycols $R_4$ is hydrogen or methyl,

A is the organic divalent radical of a diisocyanate, k is 8–100 t and p are integers of 1 to 5

X is S, $SO_2$ or NR.

It will be noted that the invention condensation polymers, being made up of blocks I and II, are of the pattern:

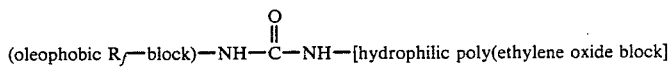

The molecular weight of Blocks I and II will vary, depending on the substituents and the number of repeating units in each. However, the advantages combination of Blocks I and II can be achieved by the use of monomer or prepolymer reactants so as to give 15–70% Block I to 30% to 85% Block II in the final polymer.

The segmented perfluoroalkyl/hydrophilic polymers are useful on substrates as coatings, which will (1) prevent, or at least reduce, soiling and (2) release soil when washed with water. They are therefore useful as ingredients in floor polishes, furniture waxers, window washing fluids, and so on; their most important application is as a soil-release finish on textiles, especially polyester/cotton textiles. Generally, they are useful as coatings on glass, ceramics, masonry, wood, plastics, textiles, leather and metals, or as additive ingredients in such coatings.

polybasic carboxylic acid, anhydride or acryl halide; phosgene; or a bischloroformate.

The polyhydroxy component can be a polyol, an $R_f$-glycol, a polyether, a polyester, an $R_f$-containing polyether, an $R_f$-containing polyester or mixture thereof.

The polyols are well-known in the urethane art and include:

Ethylene glycol, 1,3-propanediol, 1,4-butanediol, 1-5-pentanediol, 1,6-hexanediol, 1,9-nonanediol, 1,10-decanediol, di-, tri-, tetra- and pentaethylene glycol, bis(4-hydroxybutyl) ether, bis(2-hydroxyethyl) thioether, bis(4-hydroxybutyl) thioether, 1,4-bis(3-hydroxypropyl)benzene, glycerol, trimethylolpropane, 1,2,6-hexanetriol, sorbitol, mannitol, pentaerythritol, 2-ethyl-1,3-butylene glycol, octamethylene glycol, 2-ethyl-1,3-hexanediol, dodecamethylene glycol, tetradecamethylene glycol, hexadecamethylene glycol, octadecamethylene glycol.

The polyol can also contain cycloaliphatic groups, e.g. 1,4-cyclohexane-diol, 1,4-bis(hydroxymethyl)cyclohexane, 4,4'-dihydroxyl-1,1'-dicyclohexyl and the like. If desired mixtures of polyols can be used.

Polyols in addition to those described above, that are considered especially useful, are those containing tertiary nitrogen atoms which can be quaternized with acids, thereby converting a water-insoluble urethane composition into one that is water soluble or emulsifiable. Generally, an isocyanate-terminated prepolymer having a molecular weight of 200 to 10,000, preferably 400 to 4,000, is reacted with a difunctional tertiary amine to provide a segmented polymer containing tertiary nitrogen atoms. The nitrogen atoms can be quaternized, for example, by alkylation with methyl chloride or dimethyl sulfate to yield a composition that in polar media yields a dispersion in water. The polyammonium polyurethane compositions are obtained even more readily by neutralization of the basic polyurethane composition in a polar organic solvent such as acetone, methyl ethyl ketone, tetrahydrofuran, with a strong (HCl) or preferably weak (pK>4) acid such as the $C_2$-$C_9$ alkanoic acids. Acetic acid is especially preferred because the acetic acid evaporates with the water on drying to leave the water-insoluble hydrophobic starting polyurethane composition.

The neutralized polyurethane composition in a polar solvent spontaneously forms a dispersion when water is added. The solvent can thereafter be distilled off to give a solvent-free latex whose film-forming qualities are comparable to those of the organic solution.

In a convenient mode of preparing the water-dispersible basic polyurethane compositions, a polyester or polyether diol is reacted in a non-reactive polar solvent, such as acetone, methyl ethyl ketone, tetrahydrofuran and the like, with an excess of a diisocyanate such as tolylene diisocyanate or, preferably an aliphatic diisocyanate which tends to give non-yellowing urethanes such as dimer acid derived diisocyanate (DDI, commercially available from Quaker Oats Company) or another diisocyanate which is described herein as providing non-yellowing urethanes, and the prepolymer partially chain extended with an alkyl diethanolamine to yield a urethane composition containing tertiary amino groups. The urethane composition can then be acidified with a solution of aqueous weak acid (pK>4) such as acetic acid; the concentration of acid is not critical. An emulsion immediately forms when this composition is added to water.

The polyurethane compositions can contain from as little as 5 to 800 milliequivalents of ammonium groups per 100 grams of polyurethane composition, preferably from about 50 to about 500 milliequivalents of ammonium groups per 100 grams.

Some useful polyols containing tertiary nitrogen atoms can be represented by the formula

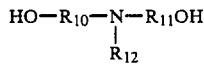

where $R_{10}$ and $R_{11}$ are alkyl of 2 to 4 carbon atoms or a group of formula

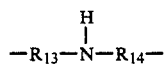

where
$R_{13}$ and $R_{14}$ are alkyl of 2 to 4 carbon atoms
$R_{12}$ is alkyl of 1 to 18 carbon atoms, cyclohexyl, tolyl, xylyl, naphthyl.

Useful polyols that contain tertiary nitrogen atoms include the alkoxylated aliphatic, cycloaliphatic aromatic and heterocyclic primary amines:
N-methyl-diethanolamine, N-butyl-diethanolamine, N-oleyl-diethanolamine, N-cyclohexyl-diethanolamine, N-methyl-diisopropanolamine, N-cyclohexyl-diisopropanolamine, N,N-dihydroxyethylaniline, N,N-dihydroxyethyl-m-toluidine, N,N-dihydroxyethyl-p-toluidine, N,N-dihydroxypropyl-naphthylamine, N,N-tetrahydroxyethyl-aminopyridine, polyethoxylated butyldiethanolamine, polypropoxylated methyldiethanolamine (molecular wt. 1000),polypropoxylated methyldiethanolamine (molecular wt. 2000), polyesters with tertiary amino groups, tri-2-hydroxypropyl-(1)-amine, N,N-di-n-(2:3-dihydroxypropyl)-amine, N,N'-bis-hydroxypropylethylenediamine, N,N'-dimethyl—N,N'-bis-(hydroxyethyl)ethylenediamine, 11-stearyldiethanolamine.

The $R_f$-glycols can be incorporated in the water-dispersible urethane compositions in an amount sufficient to provide the desired improvement in the surface properties of the polyurethane composition.

Useful polyethers are well-known and widely employed in urethane technology.

The polyethers are generally prepared commercially from lower alkylene oxides e.g. ethylene, propylene and butylene oxide and di- or polyfunctional alcohols. They have a molecular weight of from 400 to 5000. A list of commercially available polyethers, trade names, molecular weight range and suppliers can be found in Volume 11, Polyurethane, page 511, Encyclopedia of Polymer Science and Technology, John Wiley and Sons, Inc., 1969.

Hydroxy-terminated polyesters can be prepared from a polybasic acid, anhydride or aryl halide and a polyol, as described above and/or an $R_f$-glycol.

Useful dicarboxylic acids are those derived from a saturated aliphatic or cycloaliphatic dicarboxylic acid of 2 to 36 carbon atoms or an aromatic dicarboxylic acid of 8 to 18 carbon atoms, e.g. compounds of formula L(COOH)$_2$ where L is preferably alkylene of 0–16 carbon atoms or arylene of 6 to 16 carbon atoms. Such acids include oxalic, malonic, succinic, glutaric, adipic, pimelic, suberic, azelaic, sebacic, brassylic, octadecanedioic, dimer acid, 1,4-cyclohexanedicarboxylic, 4,4'-dicyclohexyl-1,1'-dicarboxylic, phthalic, isophthalic, terephthalic, methylphthalic, chlorophthalic, diphenyl-2,2'-dicarboxylic, diphenyl-4,4'-dicarboxylic, 1,4-naphthalene dicarboxylic, diphenylmethane-2,2'-dicarboxylic, diphenylmethane-3,3'-dicarboxylic, diphenylmethane-4,4'-dicarboxylic acid and the like.

Adipic acid and phthalic anhydride are the most common acid and anhydride. Of the polyols, the most commonly used include ethylene glycol, propylene glycol, 1,2-, 1,3- and 1,4-butylene glycol, 1,6-hexylene glycol, trimethylolpropane, glycerol, 1,2,6-hexanetriol and diethylene glycol.

Useful hydroxyl-terminated polyesters can also be derived from natural caster oil and glycerol, from caprolactones and ethylene glycol. Such hydroxy-terminated polyesters have hydroxyl numbers ranging from 40 to 500 and very low acid numbers ranging from 0 to 2.

Hydroxyl-terminated polycarbonates can be obtained by reacting an excess of a polyol with phosgene. Hydroxyl terminated polyether carbonates are also available and suitable for this invention.

Hydroxy-terminated polybutadienes, or butadiene styrenes and butadiene-acrylonitriles are useful herein, as are hydroxyl containing graft polymers of the polyether polyacrylonitrile type.

Any convenient isocyanate can be used to react with the R$_f$-glycol or R$_f$-containing hydroxy-terminated prepolymer. Myriads of useful isocyanates are well-known in the art. Thus, one can use aromatic isocyanates, diisocyanates, triisocyanates and polyisocyanates.

Useful aromatic diisocyanates can be represented by the formula

A(NCO)$_2$ where
A is phenylene that is unsubstituted or substituted by one or two alkyl of 1 to 4 carbon atoms, alkoxy of 1 to 4 carbon atoms, chloro, bromo and nitro, naphthylene that is unsubstituted or substituted by one or two of alkyl of 1 to 4 carbon atoms, chloro, bromo and nitro or where
A is a group of formula

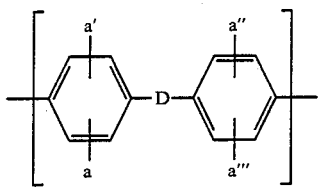

where
D is a direct bond, oxygen, methylene or ethylene and
a, a', a" and a'" each independently is hydrogen, alkyl of 1 to 4 carbon atoms, alkoxy of 1 to 4 carbon atoms, chloro or bromo.

Aromatic triisocyanates can be represented by the formula

G(NCO)$_3$ where G is the benzene or toluene group.

Aromatic di- and triisocyanates as described above include
Tolylene diisocyanate (TDI) (all isomers), 4,4'-diphenylmethane diisocyanate (MDI), tolidine diisocyanate, dianisidine diisocyanate, m-xylylene diisocyanate, p-phenylene diisocyanate, m-phenylene diisocyanate, 1-chloro-2,4-phenylene diisocyanate, 3,3'-dimethyl-4,4'-bisphenylene diisocyanate, 4,4'-bis(2-methylisocyanatophenyl)methane, 4,4'-bisphenylene diisocyanate, 4,4'-bis(2-methoxyisocyanatophenyl)methane, 1-nitro-phenyl-3,5-diisocyanate, 4,4'-diisocyanatodiphenyl ether, 3,3'-dichloro-4,4'-diisocyanatodiphenyl ether, 3,3'-dichloro,4,4'-diisocyanatodiphenylmethane, 4,4'-diisocyanatodibenzyl, 3,3'-dimethoxy-4,4'-diisocyanatodiphenyl, 2,2'-dimethyl-4,4'-diisocyanatodiphenyl, 2,2'-dichloro-5,5'-dimethoxy-4,4'-diisocyanatodiphenyl, 3,3' dichloro-4,4'-diisocyanatodiphenyl benzene-1,2,4-triisocyanate, benzene-1,3,5-triisocyanate, benzene-1,2,3-triisocyanate, toluene 2,4,6-triisocyanate, toluene 2,3,4-triisocyanate, 1,2-naphthalene diisocyanate, 4-chloro-1,2-naphthalene diisocyanate, 4-methyl-1,2-naphthalene diisocyanate, 1,5-naphthalene diisocyanate, 1,6-naphthalene diisocyanate, 1,7-naphthalene diisocyanate, 1,8-naphthalene diisocyanate, 4-chloro-1,8-naphthalene diisocyanate, 2,3-naphthalene diisocyanate, 2,7-naphthalene diisocyanate, 1,8-dinitro-2,7-naphthalene diisocyanate, 1-methyl-2,4-naphthalene diisocyanate, 1-methyl-5,7-naphthalene diisocyanate, 6-methyl-1,3-naphthalene diisocyanate, 7-methyl-1,3-naphthalene diisocyanate, polymethylene polyphenyl isocyanate and co-products of hexamethylene diisocyanate and tolylene diisocyanate.

Useful aliphatic diisocyanates include those of general formula

A(NCO)$_2$ where A is straight or branched chain alkylene of 2 to 16 carbon atoms.

Useful aliphatic or cycloaliphatic polyisocyanates include - 1,2-ethane diisocyanate, 1,3-propane diisocyanate, 1,4-butane diisocyanate, 2-chloropropane-1,3-diisocyanate, pentamethylene diisocyanate, propylene-1,2-diisocyanate, 1,6-hexane diisocyanate, 1,8-octane diisocyanate, 1,10-decane diisocyanate, 1,12-dodecane diisocyanate, 1,16-hexadecane diisocyanate and other aliphatic diisocyanates such as 1,3-cyclohexane diisocyanate, 1,4-cyclohexane diisocyanate, cyclohexane triisocyanate, 4,4'-methylene bis(cyclohexyl isocyanate).

Additionally, the following diisocyanates are particularly preferred because urethane compositions made therefrom tend to be non-yellowing:
1,6-hexamethylene diisocyanate (HDI), 2,2,4- and 2,4,4-trimethylhexamethylene diisocyanate (TMDI), dimer acid derived diisocyanate (DDI) obtained from dimerized fatty acids, such as linoleic acid 4.4'-dicyclohexylmethane diisocyanate (hydrogenated MDI), isophorone diisocyanate, 3-isocyanatomethyl-3,5,5-trimethylcyclohexyl diisocyanate, lysine methyl ester diisocyanate (LDIM), bis(2-isocyanatoethyl) fumarate (FDI),bis(2-isocyanatoethyl) carbonate, m-tetramethylxylylene diisocyanate (TMXDI), where D is the residue of a diisocyanate as described above; additional polyisocyanates include polymethylene polyphenylisocyanate (PAPI) and tris-(isocyanatophenyl) thiophosphate (Desmodur).

Additional isocyanate components can be prepared by reacting an excess of a diisocyanate as described above with a suitable hydroxyl component, such as a polyol as described above or an R$_f$-glycol as described herein, or combination thereof, to obtain an isocyanate-terminated prepolymer.

In addition to the polyisocyanate, useful urethane compositions can be obtained from the aliphatic and aromatic monoisocyanates. The low molecular weight urethane compositions obtained by reacting an R$_f$-glycol with a monoisocyanate are useful to impart soil and mold-release properties to a variety of natural and synthetic polymers.

Some useful aromatic monoisocyanates include - 2-fluorophenyl isocyanate, 3-fluorophenyl isocyanate, 4-fluorophenyl isocyanate, m-fluorosulfonylphenyl isocyanate, trans-2-phenylcyclopropyl isocyanate, m-tolyl isocyanate, p-tolyl isocyanate, α,α,α-trifluoro-o-tolyl isocyanate, α,α,α-trifluoro-m-tolyl isocyanate, p-bromophenyl isocyanate, 2,5-dimethylphenyl isocyanate, o-ethoxyphenyl isocyanate, p-ethoxyphenyl isocyanate, o-methoxyphenyl isocyanate, m-methoxyphenyl isocyanate, p-methoxyphenyl isocyanate, 1-naphthyl isocyanate, o-nitrophenyl isocyanate, m-nitrophenyl isocyanate, p-nitrophenyl isocyanate, p-phenylazophenyl isocyanate, o-tolyl isocyanate.

Useful aliphatic or cycloaliphatic monoisocyanates include such alkyl isocyanates of 1 to 16 carbon atoms as methyl isocyanate, ethyl isocyanate, n-propyl isocyanate, n-butyl isocyanate, t-butyl isocyanate, hexyl isocyanate, octyl isocyanate, dodecyl isocyanate, octadecyl isocyanate, hexadecyl isocyanate and mixtures thereof, as well as cyclohexyl isocyanate.

m-Isopropenyldimethyl benzyl isocyanato (TMI) isocyanate-terminated prepolymers typically having a molecular weight of from 200 to about 4000 can be prepared by reacting an excess of an isocyanate component with a polyhydroxy component. The isocyanate component can be a diisocyanate or polyisocyanate as previously described, or can be a low molecular weight isocyanate-terminated prepolymer.

The hydroxy component can be one or more of a polyol, polyester, polyether, polycarbonate and $R_f$-glycol, all as described previously.

It can be seen that the properties of ultimate urethane compositions can be modified by appropriate modifications in the compositions of the prepolymers.

In addition to the formation of the urethane compositions described above, the $R_f$-glycols described herein can be converted to the corresponding bischloroformate by treatment with chlorocarbonyl pyridinium chloride:

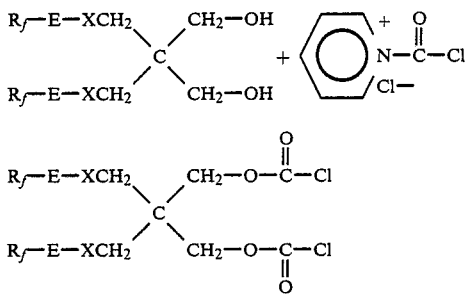

which in turn can be reacted with an appropriate amine to yield a urethane composition:

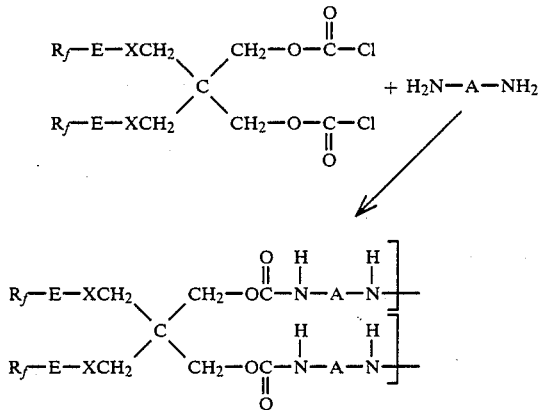

where A is a divalent organic radical as previously described.

The reaction between the isocyanate component and the hydroxyl component can be carried out in bulk, i.e., without solvent, or in the presence of non-reactive, anhydrous, organic solvents. Solvent media in which the reaction can be carried out include ketones, such as acetone, methyl ether ketone and methyl isobutyl ketone; esters such as ethyl acetate, isopropyl acetate, butyl acetate, 2-ethylhexyl acetate; hydrocarbons such as hexane, heptane, octane and higher homologs, cyclohexane, benzene, toluene, xylene or blends of aliphatic, cycloaliphatic and aromatic hydrocarbons or aprotic solvents such as N-methylpyrrolidine; It is also possible to employ ethers, both aliphatic and alicyclic including di-n-propyl ether, di-butyl ether, tetrahydrofuran and the diethers of polyalkylene oxides. In addition, chlorinated solvents such as 1,1,1-tri-chloroethane, dichloroethyl ether, ethylene dichloride, perchloroethylene and carbon tetrachloride can be used.

Among the solvents listed, the water miscible solvents such as acetone and methyl ethyl ketone are most important since they allow conversions of $R_f$-urethanes into water soluble $R_f$-urethanes as previously described.

In all cases, the solvents should be anhydrous to avoid urea formation.

The reaction can, if desired, be catalyzed and those catalysts conventionally employed in the urethane art are useful herein. Useful catalysts fall principally in two groups - a. amino compounds and other bases:
triethylamine and other trialkylamines, triethylenediamine, 1,4-diaza-2,2,2-bicyclooctane, N-(lower)alkylmorpholines, N,N,N',N'-tetramethylethylenediamine, N,N,N',N'-tetramethyl-1,3-butanediamine, substituted piperazines, dialkylalkanolamines, benzyltrimethylammonium chloride and b. organometallic and inorganic compounds:
cobalt naphthenate, stannous chloride, stannous octoate, stannous oleate, dimethyl tin dichloride, di-n-butyltin dilaurylmercaptide, tetra-n-butyl-tin, trimethyl-tin hydroxide, di-n-butyltin dilaurate.

Such catalysts may be used singly or in combination with each other. Beneficial synergistic catalysis may occur when combinations are used.

While it is possible to carry out the reaction without the use of a catalyst, it is preferable for reasons of economy and to assure a complete reaction, to utilize one or more catalysts as listed in amounts ranging from 0.001 to 1% based on the weight of the reactants. It is similarly advantageous to carry out the urethane synthesis at elevated temperature, usually between room temperature and 120° C. and preferably at 60° C. to 80° C. to obtain a complete reaction between 0.5 to 8 hours reaction time.

The reaction can be easily followed by titration of the isocyanate group or by IR analysis.

The determination of the critical surface tension ($\gamma c$) in dynes per centimeter shows that the free surface energy of a polyurethane is lowered if the novel $R_f$-glycols are incorporated into the urethane chain.

The critical surface tensions ($\gamma c$) are determined by contact angle measurements as described by W. Zisman, *Contact Angles*, Advances in Chemistry, No. 43, ACS Publications, Washington, D.C., 1964.

The usefulness of the polyurethane compositions is, conveniently shown by measuring the oil, water and soil repellency ratings of substrates such as fabrics, paper, leather, etc. which are treated with solutions or emulsions of the novel urethane compositions.

As already indicated, the urethane compositions of the invention are highly effective for imparting oil and water repellent properties to substrates to which they are applied and coatings of these polymers may be prepared by any of the well-known techniques. When prepared by bulk or suspension polymerization techniques, these urethane compositions can be applied, for example, from a dilute solution in suitable a solvent such as the fluoroalkanes, fluorochloroalkanes, fluoroalkanoic acids, chlorinated alkanes or aromatics, hydrocarbon aromatics, ketones, ester and others. Concentrations of the fluorinated polymer in the solvent can be adjusted to provide an amount of urethane composition deposited on the substrate sufficient to provide oil and water repellency. This amounts typically to a deposit of from 0.01 to 10%, preferably from 0.1 to 1%, of urethane composition, based on the weight of substrate. If the urethane composition is obtained as an aqueous latex or emulsion, the system can be diluted with water or other appropriate diluent to similarly provide an amount of urethane ranging from 0.01 to 10% of the weight of substrate deposited thereon.

The urethane solution or latex may be applied by any of the known techniques such as by dipping, spraying, brushing, padding, roll coating or by any desired combination of such techniques. The optimum method of application will depend principally on the type of substrate being coated.

Coatings of the urethane compositions of the invention may be applied to any desired substrate, porous or non-porous. They are particularly suited for application to porous materials such as textiles, leather, paper, wood, masonry, unglazed porcelain and the like to provide valuable oil and water repellency properties. However, they may also be applied to non-porous materials such as metals, plastics, glass, painted surfaces and the like to provide similar oil and water repellency properties. More specifically the urethane compositions of the invention act as levelling, wetting and spreading agents in formulations designed for application to floors, furniture and automobiles. In such applications a protective oil and water repellent film is left on the treated object after the removal of the bulk of the material. Such levelling, wetting, spreading and film forming properties are also useful in a. formulations for cleaning glass and other hard, non-porous materials b. hair care products such as rinses, shampoos and hair sprays.

c. paint, stain and varnish formulations for application to wood, masoning and ceramics.

In the treatment of paper the urethane compositions may be present as an ingredient in a wax, starch, casein, elastomer, or wet strength resin formulation. Aqueous emulsions of the urethane compositions are especially useful in the treatment of paper. By mixing the urethane compositions in an aqueous or oil type paint formulation, it may be applied effectively to unpainted asbestos siding, wood, metal and masonry. In the treatment of floors and tile surfaces and like substrates, and urethane compositions may be applied by their incorporation in an emulsion or solution.

Because of the ability of the surfaces treated with these urethane compositions to withstand abrasive action, the advantages incident to the repellency to oil and water and their resistance to soiling imparted by coating them with the urethane compositions of this invention, preferred classes of articles to be treated are papers and textiles. Illustrative papers are carbonizing tissue, wallpaper, asphalt laminates, liner board, cardboard and papers derived from synthetic fibers.

For application to textile materials such as fabrics woven and non-woven, fibers, films, yarns, cut staple, thread etc. or articles made from fabrics, fibers, films, yarns, etc. the urethane compositions of the invention are preferably prepared as aqueous latices or emulsions which are then diluted, preferably with water and applied to the textiles from pad baths which may contain other treating materials. In accordance with this technique, the fabric or the textile material is passed through the bath, passed through squeeze rolls adjusted to leave the desired amount of the latex on the fabric, dried at a temperature of about 25° to 125° C. and then cured in a curing oven at a temperature in the range of from 120° C. to 195° C. for 0.2 to 20 minutes. The weight of urethane composition deposited on the fabric may range from 0.01 to 10% of the weight of fabric. Preferably, very small amounts are used in the range of 0.1 to 1%, often from 0.1 to 0.5% to give high degrees of water and oil repellency. Any types of textile materials, such as cotton, wool, fiber glass, silk, regenerated cellulose, cellulose esters, cellulose ethers, polyesters, polyamides, polyolefins, polyacrylonitrile, polyacrylic esters, inorganic fibers, etc. either along or blended in any combination may be successfully coated with the urethane compositions of the invention. The resulting textile material will be found to be repellent to water and oil, and the textile material will retain its resistance to such agents even after many launderings and dry cleanings.

It will be often advantageous to use the urethane compositions of the invention in combination with conventional finishes, such as mildew preventatives, moth resisting agents, crease resistant resins, lubricants, softeners, fat liquors, sizes, flame retardants, antistatic agents, dye fixatives and water repellents.

TEST METHODS

The AATCC water spray test rating was determined according to Standard Test method 22-1985 of the American Association of Textile Chemists and Colorists, Volume 61, 1986 (also designated ASTM-D-583-58). Ratings are given from 0 (minimum) to 100 (maximum).

The AATCC Oil Rating was determined according to Standard Test method 118-1983 of the American Association of Textile Chemists and Colorists. Ratings are given from 0 (minimum) to 8 (maximum). A commonly accepted level of repellency for oil repellent fabrics in the United States is an oil repellency of 4.

All mentioned AATCC Tests are listed in the Technical manual of the American Association of Textile Chemists and Colorists, volume 61, edition 1986.

Polymers prepared in water or a water-solvent mixture or a solvent which is water-miscible may be applied to polyester-cotton twill by padding from an aqueous pad bath containing also the following permanent press resins, catalyst and additives (so-called permanent press recipe):

After the padding, the fabric is dried at 100° C. for 2 minutes and cured at 163° C. for 5 minutes.

The invention described above is illustrated by the following examples:

Examples 1 to 19 illustrate the preparation of the $R_f$-glycols.

Example 20 demonstrates the thermal superiority of the subject diols.

Examples 21 to 24 illustrate the preparation of polymeric compositions, and certain utilities of these compositions.

EXAMPLE 1

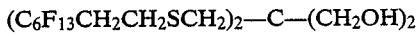

1,1,2,2-Tetrahydroperfluorooctanethiol (176.7 gm, 0.465 mol) and dibromoneopentyl glycol (60.8 gm, 0.232 mol) are reacted under nitrogen with potassium carbonate (64.3 gm 0.465 mol) and 2-pentanone (53.2 gm) as the solvent. The reaction is carried out at 105° C. for 16 hours. The product is stirred at 70° C. and washed once with 350 ml distilled water. Residual water is removed as an azeotrope and the remaining solvent is evaporated under house vacuum. The diol (187.5 gm, g4% of theory) is of 89% purity by GLC. The crude product is recrystallized twice from 500 gm toluene to give a final product 95% pure by GLC, m.p. 71.5°-73.5° C. Analysis for $C_{21}H_{18}F_{26}O_2S_2$: Calculated: C, 29.3; H, 2.1; F, 57.4., S, 7.5. Found: C, 29.4; H, 2.0; F, 56.6., S, 7.7.

EXAMPLE 2

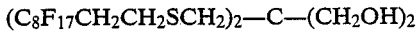

1,1,2,2-Tetrahydroperfluorooctanethiol (111.6 gm, 0.232 mol) and dibromoneopentyl glycol (30.4 gm, 0.116 mol) are reacted under nitrogen with potassium carbonate (32.1 gm, 0.232 mol) and 2-pentanone (30.7 gm) as the solvent. The reaction is carried out at 100° C. for 17 hours and the by-product salts (KBr) is removed by a hot gravity filtration. The crude product is crystallized and vacuum filtered giving 101.1 gm (82% of theory) of a pale yellow solid, 77% pure by GLC. The diol is recrystallized twice from toluene (400 g) and once from carbon tetrachloride (400 g) to give a final product of 96% purity, m.p. 90°-92.5° C. Analysis for $C_{25}H_{18}F_{34}O_2S_2$: Calculated: C, 28.3., H, 1.7., F, 60.9; S, 6.1. Found: C, 28.3., H, 1.9., F, 60.9., S, 6.5.

EXAMPLE 2a

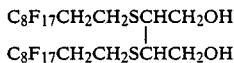

This prior art diol is prepared according to Example 2b of U.S. Pat. No. 3,935,277.

EXAMPLE 3

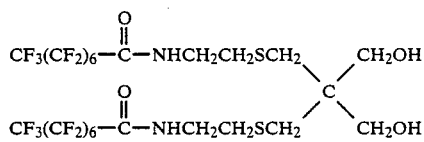

N-[2-Mercaptoethyl]-perfluoro-octanamide (45.3 gm, 0.10 mol) and dibromoneopentyl glycol (12.5 gm, 0.048 mol) are reacted under nitrogen with potassium carbonate (13.2 gm. 0.10 mol) and 2-pentanone 14.0 gm) as the solvent. The reaction is run at 103° C. for 19.5 hours. The reaction mixture is stirred at 75° C. and washed twice with 80 g distilled water. The solvent is evaporated below 115° C. to yield a brown product which is transferred as a brittle solid. This solid is recrystallized from toluene and then from ethanol to yield a white solid (32 gm, 64% of theory) which is 93% pure by GLC. NMR showed proton resonances at 2.72 ppm, 4 protons, S—$\underline{CH_2}$C: 2.79 ppm, 4 protons, $\underline{CH_2}SCH_2$; $CH_2S\underline{CH_2}$; 3.60 ppm, 4 protons, NH—$\underline{CH_2}$, 3.65 ppm, 4 protons, $\underline{CH_2}$—OH; 6.97 ppm, 1 proton, N—H.

Analysis for $C_{25}H_{20}F_{30}N_2O_4S_2$: Calculated: C, 28.7; H, 1.9; N, 2.7; F, 54.5; S, 6.1. Found: C, 28.5; H, 1.7; N, 2.8; F, 54.6; S, 6.3.

EXAMPLE 4

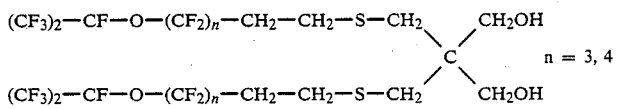

ω-Heptafluoroisopropoxy-1,1,2,2-tetrahydroperfluoroalkanethiol (consisting of 73% n=3 homolog and 27% n=4 homolog) (46.0 gm, 0.080 mol) and dibromoneopentyl glycol (10.5 gm, 0.040 mol) are reacted under nitrogen with potassium carbonate 11.1 gm, 0.080 mol) and 2-pentanone (13.0 gm) as the solvent. The reaction is carried out at 103° C. for 18 hours. The reaction mixture is stirred at 75° C. and washed twice with 80 gms distilled water. The solvent is evaporated below 115° C. to yield a yellow oil which solidifies upon cooling to a waxy yellow gel (32.3 gm, 64% of theory). The product is 87% pure by GLC. NMR confirmed structure with the general proton assignments are the same as in example 1.

Analysis for product (n=3, 4) Calculated: C, 28.1; H, 2.0; F, 55.9; S, 7.0. Found: C, 27.7; H, 1.6; F, 59.5; S, 5.3.

EXAMPLE 5

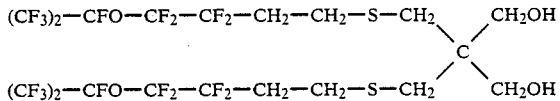

4-Heptafluoroisopropoxy-1,1,2,2-tetrahydroperfluorobutanethiol 43.7 gm, 0.13 mol) and dibromoneopentyl glycol (16.5 gm, 0.06 mol) are reacted under nitrogen with potassium carbonate (17.4 gm, 0.13 mol) and 2-pentanone (15.0 gm) as the solvent. The reaction is carried out at 103° C. for 19 hours. The product is stirred at 75° C. and washed twice with 80 ml. distilled water. The solvent is evaporated below 115° C. and the product transferred hot as a yellow oil which remains fluid. The diol (31.4 gm, 63% of theory) is of 87% 87% purity by GLC. NMR showed proton resonances at 2.01 ppm, 2 protons, -OH; 2.1-3.0 ppm, 8 protons, $CF_2CH_2CH_2S$; 2.70 ppm, 4 protons, $SCH_2C$; 3.66 ppm, 4 protons —$(CH_2—OH)_2$.

Analysis for product $C_{19}H_{18}F_{22}O_4S_2$: Calculated: C, 28.8; H, 2.3; F, 52.7; S, 8.1. Found: C, 28.9; H, 2.4; F, 50.4; S, 7.6.

EXAMPLE 6

Tetrakis-(1,1,2,2-tetrahydroperfluoroalkanethio)dipentaerythritol

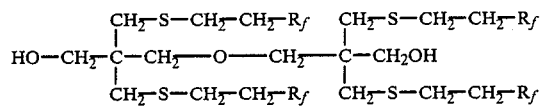

1,1,2,2-Tetrahydroperfluoroalkanethiol* (139.6 g, 0.28 mol) and sym-tetrabromodipentaerythritol (35.0 g, 0.07 mol) are reacted under nitrogen with potassium carbonate (38.7 g, 0.28 mol) and 2-pentanone (60.0 g) as the solvent. The reaction is run at 103° for 19.5 hours, and is then allowed to cool and washed twice with 160 g distilled water at 75° C. The water layer is removed and the remaining water/2-pentanone nmixture azeotroped below 115° C. The product is isolated as a brittle, yellowish-brown solid and crystallized from toluene to yield a pale yellow solid (127.4 g, 86% of theory) m.p. 79.7°–87.4° C. NMR shows proton resonances at 1.93 ppm, 2 protons, O—H; 2.40 ppm, 8 protons, $R_f$—CH$_2$—; 2.63-2.90 ppm, 16 protons, CH$_2$—S—CH$_2$; 3.43 ppm, 4 protons, CH$_2$—O—CH$_2$, 3.65 ppm, 4 protons, CH$_2$—OH.

* $R_f$ distribution C$_8$/C$_{10}$ - 88.9%/6.4%

Analysis for % OH: Calculated = 1.58%. Found = 1.56%.

EXAMPLE 7

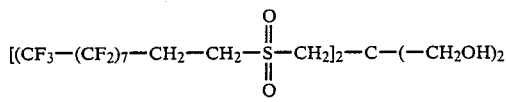

2,2-Bis(1,1,2,2-tetrahydroperfluorodecylsulfonylmethylene)-1,3-propanediol 2,2-Bis-(1,1,2,2-tetrahydroperfluorodecylthiomethylene)-1,3-propanediol (25.0 g, 0.024 mol) is dissolved in glacial acetic acid (38.09 g, 0.63 mol) and warmed to 40° C. Hydrogen peroxide (5.4 gm, 30%) is added and the mixture is stirred for 1 hour. The reaction mixture is then heated to 100° C. and additional hydrogen peroxide (10.6 g, 30%) is added. The product precipitates as a yellowish-white solid (24.6 g, 95% of theory) and is crystallized from isopropyl acetate to yield a white solid, m.p.165°–168° C. which was 92% pure by GLC. NMR shows proton resonance at 2.82 ppm, 4 protons,

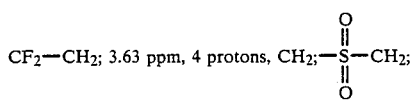

CF$_2$—CH$_2$; 3.63 ppm, 4 protons, CH$_2$;—S—CH$_2$;

3.93 ppm, 4 protons, S—CH$_2$—C—;

4.25 ppm, 4 protons, —C—CH$_2$OH.

Analysis for C$_{25}$H$_{18}$F$_{34}$O$_6$S$_2$; Calculated: C, 26.70, H, 1.6; F, 57.44; S, 5.70. Found: C, 26.60, H, 1.5; F, 54.50, S, 6.30.

EXAMPLE 8

Reaction Products of (R$_f$CH$_2$CH$_2$SCH$_2$)$_2$—C—(CH$_2$OH)$_2$ and E-Caprolactone 2,2-Bis(1,1,2,2-tetrahydroperfluoroalkylthiomethylene)-1,3-propanediol* (108.5 g, 0.10 mol) and E-caprolactone (45.7 g, 0.40 mol) are reacted under nitrogen at 75° C. for 1.5 hours in the presence of a catalytic amount of stannous octanoate. The reaction is then completed at 140° C. for 3 hours. The product is a soft waxy yellow solid of mp 28°–34° C. Comparative gel permeation chromatography (styrogel column, THF mobile phase) of the starting material and the product shows an increase in the weight average molecular weight from 1091 to 2508.

* $R_f$ distribution C$_6$F$_{13}$/C$_8$F$_{17}$-9%/88%

EXAMPLE 9

(R$_f$CH$_2$CH$_2$SCH$_2$)$_2$C(CH$_2$OH)$_2$ 1,1,2,2-Tetrahydroperfluoroalkanethiol* (215.8 g, 0.47 mmol) and dibromoneopentyl glycol (60.78 9, 0.23 mmol) are reacted under nitrogen with potassium carbonate (64.3 g, 0.465 mmol) and 2-pentanone (54 g) as the solvent. The reaction is carried out at 105° C. for 17 hours. The product is stirred at 70° C. and washed once with 350 ml distilled water. Residual water is removed as an azeotrope and the remaining solvent is evaporated under house vacuum. The diol (228.3 g, 92% of theory) is of 89% purity by GLC.

* $R_f$ distribution % C$_4$/C$_6$/C$_8$/C$_{10}$ - 0.1/9/88/1.2

EXAMPLE 9a

Dibromoneopentyl glycol is reacted with 1,1,2,2-tetrahydroperfluorodecyl amine in triethylamine as solvent at 80°–100°. The reaction is carried out for 12 hours and the product is worked up by acidification and precipitation into water. The powder is collected by filtration and dried to yield 2,2-Bis-(1,1,2,2-tetrahydroperfluorodecyliminomethylene-1,3-propanediol.

Using the methods described and by techniques similar to Examples 1–9, the following additional sulfido- and sulfone diols are prepared.

EXAMPLES 10 to 19

| Ex. | Thiol | Perfluoroalkyl Terminated Neopentyl Glycol |
| --- | --- | --- |
| 10 | CF$_3$CF$_2$CH$_2$SH | (CF$_3$CF$_2$CH$_2$SCH$_2$)$_2$C(CH$_2$OH)$_2$ |
| 11 | C$_6$F$_{13}$(CH$_2$)$_4$SH | (C$_6$F$_{13}$(CH$_2$)$_4$SO$_2$CH$_2$)$_2$C(CH$_2$OH)$_2$ |
| 12 | C$_8$F$_{17}$CH$_2$CH$_2$CH$_2$SH | (C$_8$F$_{17}$CH$_2$CH$_2$CH$_2$SCH$_2$)$_2$C(CH$_2$OH)$_2$ |
| 13 | C$_8$F$_{17}$CH$_2$CH$_2$N(CH$_3$)CH$_2$CH$_2$CH$_2$SH | (C$_8$F$_{17}$CH$_2$CH$_2$N(CH$_3$)CH$_2$CH$_2$CH$_2$SCH$_2$)$_2$C(CH$_2$OH)$_2$ |
| 14 | C$_8$F$_{17}$SO$_2$NHCH$_2$CH$_2$SH | (C$_8$F$_{17}$SO$_2$NHCH$_2$CH$_2$SCH$_2$)$_2$C(CH$_2$OH)$_2$ |
| 15 | C$_8$F$_{17}$CH$_2$CH$_2$SO$_2$NHCH$_2$CH$_2$SH | (C$_8$F$_{17}$CH$_2$SO$_2$NHCH$_2$CH$_2$SCH$_2$)$_2$C(CH$_2$OH)$_2$ |
| 16 | C$_7$F$_{15}$CONHCH$_2$CH$_2$SH | (C$_7$F$_{15}$CONHCH$_2$CH$_2$SCH$_2$)$_2$C(CH$_2$OH)$_2$ |
| 17 | CF$_3$CF$_2$CH$_2$CH$_2$SH | HO[CH$_2$C(CH$_2$SCH$_2$CH$_2$CF$_2$CF$_3$)$_2$CH$_2$O]$_2$—H |
| 18 | C$_8$F$_{17}$CH$_2$CH$_2$SH | HO[CH$_2$C(CH$_2$SO$_2$CH$_2$CH$_2$C$_8$F$_{17}$)$_2$CH$_2$O]$_2$—H |
| 19 |  | Reaction product of |
|  |  | (R$_f$CH$_2$CH$_2$SCH$_2$)$_2$C(CH$_2$OH)$_2$ and |

-continued

| Ex. | Thiol | Perfluoroalkyl Terminated Neopentyl Glycol |
|---|---|---|
| | | Σ-caprolactone |

EXAMPLE 20

Stability Comparisons of Bis-perfluoroalkylthio-Diols

Thermogravimetric analyses are run on the diols of Examples 2, 6, 7, 8 and prior art diol of Example 2a.

The instrument is run at 10° C./minute to either 350° C. or 500° C. with 100 ml/min $N_2$ or in air

| Diol of Example | DSC (Tm) | TGA (Wt. Loss) Temperature (°C.) of Indicated Weight Loss | | | | | |
|---|---|---|---|---|---|---|---|
| | | Under Nitrogen | | | Under Air | | |
| | | Init. | 10% | 50% | Init. | 10% | 50% |
| 2 | 79–86 | 150 | 251 | 295 | 150 | 237 | 285 |
| 7 | 165–168 | 195 | 286 | 328 | 185 | 260 | 309 |
| 8 | 28–34 | 150 | 293 | 340 | 150 | 265 | 316 |
| 6 | 79–87 | 180 | 315 | 356 | 185 | 285 | 335 |
| 2a | 50–84 | 50 | 180 | 255 | — | — | — |

These results indicate the thermal superiority of the subject bis-perfluoroalkylthio-neopentyl type diols. Pior art bis-perfluoroalkylthio-diols have poor thermal stability and appreciably decompose below 180° C. even under nitrogen. The subject diols as examplified above all are appreciably stable to greater than 280° C. in nitrogen, even to 260° C. in air. The weight loss of the diol of Example 2 is appreciable by TGA because of volatilization, not decomposition.

EXAMPLE 21

The diol of Example 9 (78.2 9, 0.073 mmol) is pre-dried azeotropically with 1,1,1-trichloroethane. It is then reacted with 3,3,4-trimethylhexane-1,6-diisocyanate (11.54 g, 0.055 mmol) under nitrogen in the presence of a catalytic amount of stannous octanoate (0.22 g) with 1,1,1-trichloroethane (135 g) as the solvent. The reaction mixture is heated at reflux for one hour at which time the N=C=O infrared band at 2270cm$^{-1}$ is absent. Then, dimer acid diisocyanate (27.7 g, 46 mmol) is added along with N-methyldiethanolamine (3.4 g, 28 mmol) and 1,1,1-trichloroethane (46.6 g). The mixture is kept at reflux for two hours and the reaction is again judged to be complete by the disappearance of the N=C=O infrared band. Molecular weight can be determined by gel permeation chromatography.

EXAMPLE 22

The diol of Example 6 (30.0 g, 0.014 mol) is predried azeotropically with isopropyl acetate and is then re-acted with 3,3,4-trimethylhexane-1,6-diisocyanate (2.19 g, 0.01 mol) under nitrogen in the presence of a catalytic amount of stannous octanoate (0.084 g) using isopropyl acetate (49.0 g) as the solvent. The reaction mixture was heated to 80° C. for 30 minutes and completeness of reaction is indicated by the absence of the N=C=O infrared band at 2270 cm$^{-1}$. Then, dimer acid diisocyanate (10.36 g, 0.017 mol) is added along with N-methyldiethanolamine (1.67 g, 0.014 mol) and isopropyl acetate (18.0 g). The mixture was heated at 80° C. for one hour until the reaction is judged to be complete by the absence of the N=C=O infrared band.

EXAMPLE 23

The diol of Example 6 (30.0 g, 0.014 mmol) is pre-dried azeotropically with isopropyl acetate and is then reacted with 3,3,4-trimethylhexane-1,6-diisocyanate (1.45 g., 0.007 mmol) under nitrogen in the presence of a catalytic amount of stannous octanoate (0.084 9), using isopropyl acetate (47.0 g) as the solvent. The reaction mixture is heated at 80° C. for 30 minutes and reaction is complete as indicated by the absence of the N=C=O infrared band at 2270 cm$^{-1}$ Then dimer acid diisocyanate (10.4 g, 17 mmole) is added along with N-methyldiethanolamine (1.25 g, 10 mmole) and isopropyl acetate (17.40 g). The mixture is heated at 80° C. for 1 hour and is again judged t be complete by the absence of the N=C=O infrared band.

EXAMPLE 24

The polyurethanes of Examples 21 and 23 are compared to an identical formulation prepared from a prior art diol.

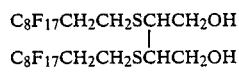

This prior art diol is prepared according to Example 2b of to U.S. Pat. No. 3,935,277.

The polyurethane products are applied by pad application with 1,1,1-trichloroethane on both 65/35 polyester/cotton poplin and 100% nylon taffeta in such a way that 0.06% F is applied to the polyester/cotton and 0.04% F to the nylon. The products are evaluated after air drying and curing in a hot air oven at >150° C. for 3 minutes. The products prepared from the subject diols have significantly improved water repellency over the prior art diol.

| Product of Example | 65/35 polyester/cotton at 0.06% F Air Dried/Oven Cured | | 100 nylon taffeta at 0.04% F Air Dried |
|---|---|---|---|
| | AATCC Oil | AATCC Spray | AATCC Spray |
| 21 | — | — | 100 |
| 23 | 4 | 100 | 100 |
| 2a (prior-art) | 4 | 80+ | 80− |

What is claimed is:
1. A compound of formula I

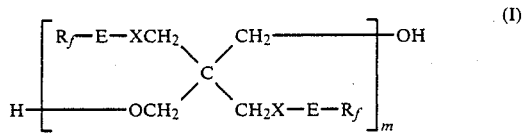

wherein
$R_f$ is a straight or branched chain perfluoroalkyl of 1 to 18 carbon atoms or said perfluoroalkyl substituted by perfluoroalkoxy of 2 to 6 carbon atoms,
E is branched or straight chain alkylene of 1 to 10 carbon atoms or said alkylene interrupted by one to three groups selected from the group consisting of —NR—, —O—, —S—, —SO$_2$—, —COO—, —OOC—, —CONR— and —SO$_2$NR—, X is —S— or —SO$_2$—, and where R is independently hydrogen, alkyl of 1 to 6 carbon atoms or hydroxyalkyl of 1 to 6 carbon atoms, and m is 1 to 3.

2. A compound of formula I according to claim 1 where $R_f$ is perfluoroalkyl of 2 to 12 carbon atoms or perfluoroalkyl of 2 to 6 carbon atoms substituted by perfluoroalkoxy of 2 to 6 carbon atoms, E is alkylene of 2 to 6 carbon atoms, —CONHCH$_2$CH$_2$—, —CH$_2$CH$_2$N(CH$_3$)CH$_2$CH$_2$—, CH$_2$CH$_2$SO$_2$NHCH$_2$CH$_2$—, or —SO$_2$NHCH$_2$CH$_2$—, X is —S— or —SO$_2$—, and m is 1 or 2.

3. A compound of formula I according to claim 1 wherein $R_f$ is perfluoroalkyl of 6 to 12 carbon atoms, E is ethylene, X is —S—, and m is 1.

4. A compound of formula I according to claim 1 wherein $R_f$ is perfluoroalkyl of 6 to 12 carbon atoms, E is ethylene, X is —S—, and m is 2.

5. A compound according to claim 1 which is (C$_6$F$_{13}$CH$_2$CH$_2$SCH$_2$)$_2$C(CH$_2$OH)$_2$.

6. A compound according to claim 1 which is (C$_8$F$_{17}$CH$_2$CH$_2$SCH$_2$)$_2$C(CH$_2$OH)$_2$.

7. A compound according to claim 1 which is (C$_7$F$_{15}$CONHCH$_2$CH$_2$SCH$_2$)$_2$C(CH$_2$OH)$_2$.

8. A compound according to claim 1 which is [(CF$_3$)$_2$CFO(CF$_2$)$_n$CH$_2$CH$_2$SCH$_2$]$_2$C(CH$_2$OH)$_2$ where n is 3 or 4.

9. A compound according to claim 1 which is [(CF$_3$)$_2$CFOCF$_2$CH$_2$CH$_2$SCH$_2$]$_2$C(CH$_2$OH)$_2$.

10. A compound according to claim 1 which is HO[CH$_2$C(CH$_2$SCH$_2$CH$_2$R$_f$)$_2$CH$_2$O]$_2$H where $R_f$ is a mixture of C$_8$F$_{17}$ and C$_{10}$F$_{21}$.

11. A compound according to claim 1 which is (C$_8$F$_{17}$CH$_2$CH$_2$SO$_2$CH$_2$)$_2$C(CH$_2$OH)$_2$.

12. A compound according to claim 1 which is (R$_f$CH$_2$—CH$_2$SCH$_2$)$_2$C(CH$_2$OH)$_2$ where $R_f$ is a mixture of C$_4$F$_9$, C$_6$F$_{13}$, C$_8$F$_{17}$, and C$_{10}$F$_{21}$.

* * * * *